United States Patent [19]

Mundhenke et al.

[11] 4,391,991

[45] Jul. 5, 1983

[54] PROCESS FOR THE PREPARATION OF PARA-FLUOROANILINE

[75] Inventors: Rudolph F. Mundhenke, North Tonawanda; Michael J. Fifolt, Grand Island, both of N.Y.

[73] Assignee: Occidental Chemical Corporation, Niagara Falls, N.Y.

[21] Appl. No.: 316,199

[22] Filed: Oct. 29, 1981

[51] Int. Cl.³ .............................................. C07C 85/00
[52] U.S. Cl. ................................................... 564/412
[58] Field of Search ......................................... 564/412

[56] References Cited

U.S. PATENT DOCUMENTS

| | | | |
|---|---|---|---|
| 3,558,707 | 1/1971 | Churchill et al. | 564/412 |
| 3,580,951 | 5/1971 | Churchill et al. | 564/412 |
| 3,639,482 | 2/1972 | Churchill et al. | 564/412 |
| 3,900,519 | 8/1975 | Gay et al. | 564/412 |
| 3,910,985 | 10/1975 | Montisn et al. | 564/412 X |
| 4,145,364 | 3/1979 | Mulvey et al. | 564/412 X |

OTHER PUBLICATIONS

Patrick et al., "J. Org. Chem.", 39(12), p. 1758, 1974.
Titov et al., "Zhur Obsachei. Khim.", 23, p. 346, 1953.

*Primary Examiner*—Paul F. Shaver
*Attorney, Agent, or Firm*—James F. Tao; Arthur S. Cookfair

[57] ABSTRACT

Para-fluoroaniline is prepared by reaction of N-phenylhydroxylamine with anhydrous hydrogen fluoride at atmospheric pressure and reflux conditions.

8 Claims, No Drawings

PROCESS FOR THE PREPARATION OF PARA-FLUOROANILINE

BACKGROUND OF THE INVENTION

This invention relates to a method for the preparation of p-fluoroaniline.

Parafluoroaniline is a commercially available compound, useful as a chemical intermediate in the preparation of dyestuffs, pesticides and pharmaceuticals.

The use of p-fluoroaniline as a starting material for the preparation of pharmaceuticals (anti-inflammatory compounds) is described in U.S. Pat. Nos. 3,681,445 and 3,692,821.

Prior art methods for the preparation of p-fluoroaniline include the following: U.S. Pat. Nos. 2,198,249; 2,884,458; 3,639,482 and 3,558,707 disclose the preparation of p-fluoroaniline by catalytic hydrogenation of nitrobenzene. U.S. Pat. No. 3,910,985 teaches the conversion of nitrobenzenes to 4-fluoroanilines by treatment with hydrogen and hydrogen fluoride. U.S. Pat. No. 4,145,364 disclose the preparation of p-fluoroaniline by treatment of phenylazide with hydrogen fluoride.

It has also been disclosed in the chemical literature that moderate yields of p-fluoroaniline may be achieved by the low temperature reaction of anhydrous hydrogen fluoride with N-phenylhydroxylamine. See Patrick et al, J. Organic Chemistry 39 (12), 1758 (1974); and Titov et al, Zhur Obshchei. Khim., 23, 346 (1953). Other investigators have suggested a mechanism for the reaction wherein p-fluoroaniline is prepared by catalytic reduction of nitrobenzene in anhydrous hydrogen fluoride. The suggested mechanism, according to Fieller et al, J. Org. Chem 26, 4014 (1961), involves the reduction of nitrobenzene to N-phenylhydroxylamine followed by the in-situ rearrangement of the latter in hydrogen fluoride.

Although p-fluoroaniline may be produced by various prior art processes, such processes are typically characterized by low yields, unwanted by-products, and/or uneconomical process conditions. It will be appreciated that further improvements in the efficiency and economy of preparation and yield and purity of the desired product, p-fluoroaniline are desirable.

SUMMARY OF THE INVENTION

This invention provides an improved process for the preparation of p-fluoroaniline by reaction of N-phenylhydroxylamine with anhydrous hydrogen fluoride at atmospheric pressure and at reflux conditions. The temperature at reflux conditions will typically be at or near 20° C.—the approximate boiling point of anhydrous hydrogen fluoride. Among the specific advantages afforded by the process of this invention are the achievement of yields up to about 90% based on N-phenylhydroxylamine, and a minimization of the formation of unwanted by-products.

In the process, an excess of hydrogen fluoride is employed, within that broad consideration, the ratio of reactants may vary, but is preferably in the range of HF:N-phenylhydroxylamine of about 5:1 to about 40:1, and most preferably about 15:1 to about 25:1. It has been found that at ratios of below about 10:1 the yield of p-fluoroaniline product is sharply reduced. Ratios above about 25:1 are generally less economical and provide little or no increase in yield.

The reaction may be run neat or with the aid of a suitable solvent. It has been found that an organic solvent may be employed effectively to improve contact of the reactants, mixing and uniformity of temperature of the reaction mixture. Suitable solvents, include, for example, methylene chloride, chloroform, carbon tetrachloride and other organic solvents that are substantially non-reactive with respect to hydrogen fluoride and N-phenylhydroxylamine, and capable of dissolving the latter, and preferably have an atmospheric pressure boiling point of above about 30° Celsius and most preferably about 35° to about 65° Celsius.

In a preferred embodiment of the invention, the solvent is one in which hydrogen fluoride is substantially insoluble, preferably methylene chloride, and the process comprises adding a solution of N-phenylhydroxylamine to liquid hydrogen fluoride.

The process of this invention is carried out under non-reducing conditions, that is, in the substantial absence of elemental hydrogen, with the resultant advantage that the formation of undesired by-products, such as aniline, is minimized.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

One hundred-twenty parts of anhydrous hydrogen fluoride was charged to reaction vessel and maintained at about 10° C. while a solution of 16.38 parts of N-phenylhydroxylamine in 280 parts of methylene chloride was added over a 10 minute period. The mixture was then heated to reflux, stirred and maintained at reflux for about 23 hours. The excess hydrogen fluoride was then removed by distillation. The reaction mixture was cooled slightly and ammonia was added to adjust the pH of the mixture to about 9. The reaction mixture was then filtered, the solid washed with methylene chloride and further purified by distillation to yield 13.6 parts of p-fluoroaniline—a yield of 89% based on N-phenylhydroxylamine.

EXAMPLE 2

To a reaction vessel, cooled to about −78° C. was added 2.73 parts of N-phenylhydroxylamine. Twelve parts of hydrogen fluoride was added and the mixture was heated rapidly to reflux and maintained thereat for about 4 hours. The bath temperature was then raised to about 60° C. and the excess hydrogen fluoride was removed by distillation. The mixture was then cooled, diluted with 66.8 parts of methylene chloride; and ammonia was added in an amount sufficient to raise the pH to greater than 10. A yield of 2.4 parts of p-fluoroaniline was obtained—a yield of 86.4% based on N-phenylhydroxylamine.

EXAMPLE 3

Twenty parts of anhydrous hydrogen fluoride was charged to reaction vessel and maintained at about −20° C. A solution of 2.73 parts of N-phenylhydroxylamine in 67 parts of methylene chloride at 3° to 8° C. was added over an 8 minute period. The mixture was then heated to reflux and maintained at reflux with stirring for about 22 hours. The excess hydrogen fluoride was then removed by distillation. The reaction mixture was cooled slightly and ammonia was added to adjust the pH of the mixture to about 9. The reaction mixture was then filtered. The solid was washed with methylene chloride and the solvent removed by distillation yielding 2.9 parts of crude products. Analysis by gas chromatographic techniques indicated a yield of 2.4 parts of p-fluoroaniline—a yield of 86.4% based on N-phenylhydroxylamine.

The general procedure of Example 2 was repeated except that the mole ratios of reactants were varied as shown in Table I, below:

TABLE I

| | | Reaction of N—phenylhydroxylamine with HF at reflux conditions | | | | |
|---|---|---|---|---|---|---|
| Bath | Time | Moles | | % yield based on N—phenylhydroxylamine | | |
| Temp °C. | Hrs. | N—phenylhydroxylamine | HF | p-Fluoroaniline | Aniline | Azoxybenzene |
| 35 | 4 | .025 | .375 | 67 | .68 | 6.4 |
| 35 | 4 | .025 | .5 | 79.1 | 0 | trace |
| 35 | 4 | .025 | .60 | 86.4 | 0 | trace |
| 35 | 4 | .025 | .45 | 72.4 | 0 | trace |
| 35 | 2 | .025 | .60 | 80.0 | 0 | trace |
| 35 | .2 | .150 | 3.6 | 81.8 | 0 | .15 |

What is claimed is:

1. A process for the preparation of para-fluoroaniline comprising reacting N-phenylhydroxylamine with anhydrous hydrogen fluoride at atmospheric pressure and reflux conditions.

2. A process according to claim 1 wherein the reactants are employed in a molar ratio of HF:N-phenylhydroxylamine of about 5:1 to about 40:1.

3. A process according to claim 1 wherein the reactants are present in a molar ratio of HF:N-phenylhydroxylamine of about 15:1 to about 25:1.

4. A process according to claim 2 carried out in the presence of a solvent.

5. A process according to claim 4 wherein the solvent is methylene chloride.

6. A process according to claim 1 wherein N-phenylhydroxylamine, dissolved in a solvent, is added to liquid hydrogen fluoride and the resultant reaction mixture is heated to reflux condition.

7. A process according to claim 6 wherein the solvent is methylene chloride.

8. A process according to claim 7 wherein the ratio of HF:N-phenylhydroxylamine is about 15:1 to about 25:1.

* * * * *